(12) United States Patent
Harding et al.

(10) Patent No.: US 8,182,636 B2
(45) Date of Patent: May 22, 2012

(54) ELECTROCHEMICAL CELL AND METHOD OF MAKING AN ELECTROCHEMICAL CELL

(75) Inventors: Ian Harding, Wells (GB); Sridhar G. Iyengar, Salem, NH (US); Marina T. Larson, Summit County, CO (US); Carl Oppedahl, Summit County, CO (US)

(73) Assignee: AgaMatrix, Inc., Salem, NH (US)

( * ) Notice: Subject to any disclaimer, the term of this patent is extended or adjusted under 35 U.S.C. 154(b) by 0 days.

(21) Appl. No.: 13/052,605

(22) Filed: Mar. 21, 2011

(65) Prior Publication Data

US 2011/0173801 A1    Jul. 21, 2011

Related U.S. Application Data

(62) Division of application No. 10/908,656, filed on May 20, 2005.

(60) Provisional application No. 60/521,555, filed on May 21, 2004.

(51) Int. Cl.
*B32B 38/04* (2006.01)
*G01N 27/327* (2006.01)

(52) U.S. Cl. .... 156/256; 156/250; 156/263; 204/403.02

(58) Field of Classification Search ............. 204/403.01, 204/403.02, 403.03; 156/250, 256, 263
See application file for complete search history.

(56) References Cited

U.S. PATENT DOCUMENTS

| | | | |
|---|---|---|---|
| 4,318,784 A | 3/1982 | Higgins et al. | |
| 4,526,661 A | 7/1985 | Steckhan et al. | |
| 4,545,382 A | 10/1985 | Higgins et al. | |
| 4,711,245 A | 12/1987 | Higgins et al. | |
| 4,942,127 A | 7/1990 | Wada et al. | |
| 5,264,103 A | 11/1993 | Yoshioka et al. | |
| 5,410,059 A | 4/1995 | Fraser et al. | |
| 5,437,999 A | 8/1995 | Diebold et al. | |
| 5,589,326 A | 12/1996 | Deng et al. | |
| 5,710,011 A | 1/1998 | Forrow et al. | |
| 5,846,702 A | 12/1998 | Deng et al. | |
| 5,876,952 A | 3/1999 | Shieh | |
| 5,942,102 A | 8/1999 | Hodges et al. | |
| 6,004,441 A | 12/1999 | Fujiwara et al. | |
| 6,129,823 A | 10/2000 | Hughes et al. | |
| 6,174,420 B1 * | 1/2001 | Hodges et al. | 204/403.14 |
| 6,262,264 B1 | 7/2001 | Buck, Jr. et al. | |

(Continued)

FOREIGN PATENT DOCUMENTS

JP    5-196596    8/1993

(Continued)

*Primary Examiner* — Kaj K Olsen
(74) *Attorney, Agent, or Firm* — Larson & Anderson, LLC

(57) ABSTRACT

Electrochemical test cells are made with precision and accuracy by adhering an electrically resistive sheet having a bound opening to a first electrically conductive sheet. A notching opening is then punched through the electrically resistive sheet and the first electrically conductive sheet. The notching opening intersects the first bound opening in the electrically resistive sheet, and transforms the first bound opening into a notch in the electrically resistive sheet. A second electrically conductive sheet is punched to have a notching opening corresponding to that of first electrically conductive sheet, and this is adhered to the other side of the electrically resistive sheet such that the notching openings are aligned. This structure is cleaved from surrounding material to form an electrochemical cell that has a sample space for receiving a sample defined by the first and second conductive sheets and the notch in the electrically resistive sheet.

18 Claims, 19 Drawing Sheets

U.S. PATENT DOCUMENTS

| | | |
|---|---|---|
| 6,294,062 B1 | 9/2001 | Buck, Jr. et al. |
| 6,352,824 B1 | 3/2002 | Buck, Jr. et al. |
| 6,551,494 B1 | 4/2003 | Feldman et al. |
| 6,558,528 B1 * | 5/2003 | Matzinger ............ 205/777.5 |
| 6,576,101 B1 | 6/2003 | Heller et al. |
| 6,605,201 B1 | 8/2003 | Mao et al. |
| 6,977,032 B2 | 12/2005 | Hasegawa et al. |
| 2004/0026244 A1 | 2/2004 | Hodges et al. |
| 2004/0217016 A1 | 11/2004 | Khan |
| 2005/0069892 A1 | 3/2005 | Iyengar et al. |
| 2005/0284758 A1 | 12/2005 | Funke et al. |
| 2006/0042941 A1 | 3/2006 | Kusaka et al. |

FOREIGN PATENT DOCUMENTS

| | | |
|---|---|---|
| WO | 0175438 A2 | 10/2001 |
| WO | 03043945 A1 | 5/2003 |

* cited by examiner

ELECTROCHEMICAL CELL AND METHOD OF MAKING AN ELECTROCHEMICAL CELL

This application is a divisional of application Ser. No. 10/908,656 filed on May. 20, 2005 and claims the benefit of U.S. Provisional Application Ser. No. 60/521,555, filed May 21, 2004, which is incorporated herein by reference.

BACKGROUND OF THE INVENTION

This invention relates to electrochemical cells and methods of making electrochemical cells for detecting the presence of, measuring the amount of, and/or monitoring the level of one or more components in a liquid sample. The cells perform an electrochemical measurement by evaluating an electrochemical parameter (i.e., potential, current, resistance, etc) between two or more electrodes which are in contact with a sample. Electrode sensors typically include a working electrode and either a counter or a reference/counter ("reference") electrode.

While use may be made of this invention in the chemical industry, especially where complex mixtures are encountered (e.g. in food chemistry or biochemical engineering) it is of particular value in biological investigation and control techniques. More particularly, it lends itself to animal or human medicine, and in particular to in vitro measuring or monitoring of components in body fluids. For convenience, the invention will be described with reference to one such procedure, the determination of glucose within a human.

In order to effectuate a measurement of glucose in a human, a sample of blood is drawn from a test subject and the sample mixed with a reagent typically comprising an enzyme and a redox mediator. The chemistry used in such a measuring device is typically:

glucose+$GOD_{ox}$--->gluconolactone+$GOD_{red}$

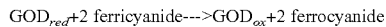

$GOD_{red}$+2 ferricyanide--->$GOD_{ox}$+2 ferrocyanide where $GOD_{ox}$ is the enzyme glucose oxidase in its oxidized state, and $GOD_{red}$ is the enzyme in a reduced state. Ferricyanide ($[Fe(CN)_6]^{3-}$) is the oxidized mediator which oxidizes $GOD_{red}$ so it can oxidize further glucose molecules. Ferrocyanide ($[Fe(CN)_6]^{4-}$) is the reduced form of the mediator which transfers electrons to an electrode (thereby regenerating ferricyanide). Thus, the generation of ferrocyanide (measured electrochemically) indicates the concentration of glucose in the sample. Other enyzmes, such as glucose dehydrogenase, have also been used.

Because glucose monitoring for diabetics is preferably done several times a day, and because each test using conventional apparatus for home use requires a finger stick to obtain blood or interstitial fluid, the developmental pressure has been towards apparatus with ever increasing convenience to the user and lower cost. As a result, electrochemical cells with small sample test volumes have been disclosed. See, for example U.S. Pat. Nos. 6,576,101; 6,551,494; 6,129,823 and 5,437,999. As the size of the sample cell becomes smaller, however, the percentage change in electrode area and cell volume resulting from a small error in manufacturing tolerance becomes greater. This is significant because the magnitude of the signal may depend on the electrode area and cell volume. Thus, stricter manufacturing controls may be required in order to achieve the necessary precision in cell size, but these stricter controls are not compatible with the goal of reduced cost.

SUMMARY OF THE INVENTION

In a first aspect, the present invention provides a simple method for producing electrochemical cells that is particularly applicable to the manufacture of cells with small and consistent sample volumes and electrode areas. The resulting electrochemical cell comprises opposing first and second electrodes separated by an electrically resistive sheet. The method comprises the steps of:

(a) forming a first bound opening in an electrically resistive sheet thereby forming a punched electrically resistive sheet;

(b) adhering the punched electrically resistive sheet to a first electrically conductive sheet thereby forming a combined sheet, wherein a first portion of a conductive surface of the first electrically conductive sheet is exposed through the first bound opening, and a second portion of the conductive surface of the electrically conductive sheet is exposed either through a second bound opening in the electrically resistive sheet or as an extension beyond an edge of the electrically resistive sheet;

(c) punching a notching opening through the electrically resistive sheet and the first electrically conductive sheet of the combined sheet, wherein the notching opening intersects the first bound opening in the electrically resistive sheet thereby transforming the first bound opening into a notch in the electrically resistive sheet, and punching a first contact area opening through the second exposed portion of the electrically conductive sheet visible to form a first electrical contact, thereby forming a punched combined sheet;

(d) punching a second electrically conductive sheet with a punch or punches to form an electrically conductive sheet having a notching opening corresponding to that of the punched combined sheet and a second contact area in the second electrically conductive sheet, thereby forming an opposite electrode sheet;

(e) adhering the opposite electrode sheet to the electrically resistive sheet portion of the punched combined sheet with an electrically conductive surface facing the electrically resistive sheet, said opposite electrode sheet being adhered such that the notching opening corresponding to the notching opening in the combined sheet is aligned with the notching opening in the combined sheet, and the second contact area is aligned with the second bound opening, thereby forming an electrochemical sheet, and (f) cleaving the electrochemical sheet thereby forming a spent electrochemical sheet and a free electrochemical cell having a sample space for receiving a sample defined by the first and second conductive sheets and the notch in the electrically resistive sheet, and first and second contact areas in electrically-conductive contact with electrode portions of the first and second conductive sheets exposed in the sample space for connection of said first and second electrode portions with a meter.

If appropriate for the test strip being made, reagent can be added during the construction of the test strip as described above.

In a preferred embodiment, both ends of the first major open area are cut in step (c) to form a sample space that is open at both ends, and defined on the sides. One opening of the sample space is at the outer edge of the sample-collection tip of the device and the other opening adjoins a hole formed near the tip of the device.

The method of the invention provides numerous advantages over prior art methods for the construction of electrochemical cells. First, the method utilizes only a limited number of sheets of material that can be the same size, and significantly larger than the cells as finally made. Second, the method of the invention does not require any printing or lithography techniques to define the sample space volume and the electrode area or to form the electrode leads and connections. Third, because the significant dimensions of the device can be defined by die cutting or similar punching operations, both the accuracy and precision of the manufacturing process is good using macroscopic processes. This allows the manufacture of electrochemical cells that operate with very small sample volumes, without substantial increase in manufacturing expense. Fourth, electrochemical cells made using the method of the invention have reduced electrode "edge" effects which reduce the accuracy of the cell. Thus, the method of the present invention provides a cost effective and therefore disposable (single use) electrochemical cell that demonstrates remarkable accuracy in measurements while requiring only a minimal amount of sample.

Practicing this method results in an electrochemical cell of simple construction. Thus, in a further aspect of the invention, there is provided an electrochemical cell having a sample-receiving end and a connector end comprising, in sequence:

(a) a first substrate, having an unpatterned layer of conductive material applied to a first surface thereof;

(b) an electrically-resistive middle layer, and (c) a second substrate, having an unpatterned layer of conductive material applied to a first surface thereof;

wherein the first surface of the first substrate and the first surface of the second substrate are adhered to the electrically resistive middle layer;

wherein the cell has a hole disposed near the sample receiving end, but spaced away from the free edge of the cell, said hole passing through the first substrate, the electrically resistive middle layer, and the second substrate, wherein the cell has a sample space, said sample space passing through electrically resistive middle layer and being bounded on opposing sides by the unpatterned conductive materials of the first substrate and the unpatterned conductive material of the second substrate and said sample space extending from the free edge of the cell to the hole and being open at both ends. Where appropriate to the cell being made, the electrochemical cell may also include a reagent in the sample space.

DETAILED DESCRIPTION OF THE INVENTION

Figure 1A:
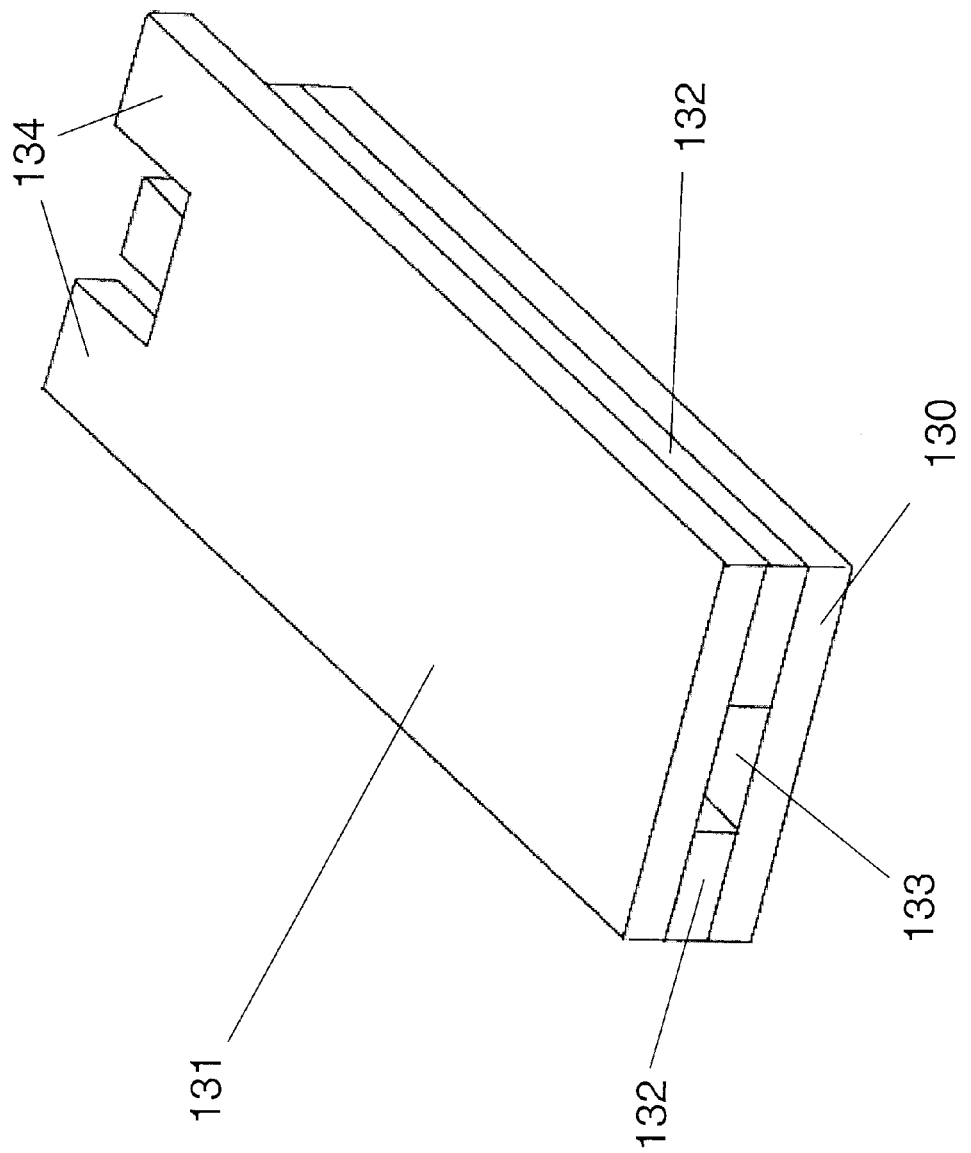
FIGS. 1A and B shows an isometric view of an electrochemical cell produced by the method of this invention.

In accordance with an embodiment of the present invention a method is provided for manufacturing of electrochemical cells comprising the steps of:

(a) punching one or more bound openings into an electrically resistive sheet thereby forming a punched electrically resistive sheet, said one or more bound openings defining a first and a second major open areas, (b) adhering the punched electrically resistive sheet to a first electrically conductive sheet thereby forming a combined sheet, wherein a conductive surface of the first electrically conductive sheet is visible through the one or more openings in the punched electrically resistive sheet, (c) punching a notching opening through the electrically resistive sheet and the first electrically conductive sheet of the combined sheet, wherein the notching opening intersects the first major area in the electrically resistive sheet thereby transforming the first major open area into a notch in the electrically resistive sheet, and punching a first contact area opening through the portion of the electrically conductive sheet visible through the second major open area of the electrically resistive sheet to form a first electrical contact, thereby forming a punched combined sheet;

(d) punching a second electrically conductive sheet with a punch or punches to form an electrically conductive sheet having a notching opening corresponding to that of the punched combined sheet and a second contact area in the second electrically conductive sheet, thereby forming an opposite electrode sheet;

(e) adhering the opposite electrode sheet to the electrically resistive sheet portion of the punched combined sheet with an electrically conductive surface facing the electrically resistive sheet, said opposite electrode sheet being adhered such that the opening corresponding to the notching opening in the combined sheet is aligned with the notching opening in the combined sheet, and the second contact area is aligned with the second bound opening, thereby forming an electrochemical sheet, and (f) cleaving the electrochemical sheet thereby forming a spent electrochemical sheet and a free electrochemical cell having a sample space for receiving a sample defined by the first and second conductive sheets and the notch in the electrically resistive sheet, and first and second contact areas in electrically-conductive contact with electrode portions of the first and second conductive sheets exposed in the sample space for connection of said first and second electrode portions with a meter.

Definitions

Numerical values in the specification and claims of this application should be understood to include numerical values which are the same when reduced to the same number of significant figures and numerical values which differ from the stated value by less than the experimental error of conventional measurement technique of the type described in the present application to determine the value.

As used in the specification and claims of this application, the following terms are used and should be understood as follows:

The term "analyte" as used in the specification and claims of this application means a component of a sample to be measured. Non-limiting examples of specific analytes include glucose, hemoglobin, cholesterol, and vitamin C.

The term "redox mediator" as used in the specification and claims of this application means a chemical species, other than the analyte, that is oxidized and/or reduced in the course of a multi-step process transferring electrons to or from the analyte to an electrode of the electrochemical cell. Non-limiting examples of mediators include:
ferricyanide
[FeIII(CN)5(ImH)]$^{2-}$
[FeIII(CN)5(Im)]$^{3-}$
[RuIII(NH3)5(ImH)]$^{3+}$
[RuIII(NH3)5(Im)]$^{2+}$
[FeII(CN)5(ImH)]$^{3-}$
[RuII(NH3)5(Im)H]$^{2+}$
[(NC)5FeII(Im)RuIII(NH3)5]$^{-}$
[(NC)5FeIII(Im)RuIII(NH3)5]$^{0}$
[(NC)5FeII(Im)RuII(NH3)5]$^{2-}$
Ferrocene (Fc) and derivatives including but not limited to:
Ferrocene monosulphonate
Ferrocene disulphonate
FcCO$_2$H
FcCH2CO$_2$H
FcCH:CHCO$_2$H
Fc(CH$_2$)$_3$CO$_2$H
Fc(CH$_2$)$_4$CO$_2$H
FcCH$_2$CH(NH$_2$)CO$_2$H
FcCH$_2$SCH$_2$CH(NH$_2$)CO$_2$H
FcCH$_2$CONH$_2$
Fc(CH$_2$)$_2$CONH$_2$
Fc(CH$_2$)$_3$CONH$_2$
Fc(CH$_2$)$_4$CONH$_2$
FcOH
FcCH$_2$OH
Fc(CH$_2$)$_2$OH
FcCH(Me)OH
FcCH$_2$O(CH$_2$)$_2$OH
1,1'-Fc(CH$_2$OH)$_2$
1,2-Fc(CH$_2$OH)$_2$
FcNH$_2$
FcCH$_2$NH$_2$
Fc(CH$_2$)$_2$NH$_2$
Fc(CH$_2$)$_3$NH$_2$
1,1'-Me$_2$FcCH$_2$NH$_2$
FcCH$_2$NMe$_2$
(R)-FcCH(Me)NMe$_2$
(S)-FcCH(Me)NMe$_2$
1,2-Me$_3$SiFcCH$_2$NMe$_2$
FcCH$_2$NMe$_3$
FcCH$_2$NH(CH$_2$)$_2$NH$_2$
1,1'-Me$_2$FcCH(OH)CH$_2$NH$_2$
FcCH(OH)CH$_2$NH$_2$
FcCH:CHCH(OH)CH$_2$NH$_2$
Fc(CH$_2$)$_2$CH(OH)CH$_2$NH$_2$
FcCH$_2$CH(NH$_2$)CH$_2$OH
FcCH$_2$CH(CH$_2$NH$_2$)CH$_2$OH
FcCH$_2$NH(CH$_2$)$_2$OH
1,1'-Me$_2$FcCHOCONHCH$_2$
FcCH(OH)(CH$_2$)$_2$NH$_2$
1,1'-Me$_2$FcCH(OH)CH$_2$NHAc
FcB(OH)$_3$
FcC$_6$H$_4$OPO$_3$Na$_2$
Osmium II and Osmium III tris(phenanthroline) (i.e. Os-phen) complexes including but not limited to:
Os(4,7-dmphen)$_3$
Os(3,4,7,8-tmphen)$_3$
Os(5,6-dmphen)$_3$
Os(bpy)$_3$Cl$_2$
Os(5-mphen)$_3$
Os(5-Cl-phen)$_3$
Os-(5-NO$_2$-phen)$_3$
Os(5-phphen)$_3$
Os(2,9-dm-4,7-dpphen)$_3$
and isostructural ruthenium complexes including but not limited to:
Ru(4,7-dmphen)$_3$
Ru(3,4,7,8-tmphen)$_3$
Ru(5-mphen)$_3$
Ru(5,6-dmphen)$_3$
Ru(phen)$_3$
[Ru(4,4'-diNH$_2$-bipy)3]$^{2+}$
Osmium II and Osmium III tris(bipyridyl) complexes (i.e. Os(bpy)$_3$) including but not limited to:
Os(bpy)$_3$
Os(dmbpy)$_3$
and related ruthenium complexes, e.g.:
Ru(bpy)$_3$
Ru(4,4'-diNH$_2$-bpy)$_3$
Ru(4,4'-diCO$_2$Etbpy)$_3$
Osmium II and Osmium III bis(bipyridyl) (i.e. Os(bpy)$_2$) complexes with other ligands including but not limited to:
Os(bpy)$_2$dmbpy
Os(bpy)$_2$(HIm)$_2$
Os(bpy)$_2$(2MeHIm)$_2$
Os(bpy)$_2$(4MeHIm)$_2$
Os(dmbpy)$_2$(HIm)$_2$
Os(bpy)$_2$Cl(HIm)
Os(bpy)$_2$Cl(1-MeIm)
Os(dmbpy)$_2$Cl(HIm)
Os(dmbpy)$_2$Cl(1-MeIm)
and related ruthenium complexes, e.g.:
Ru(bpy)$_2$(5,5'diNH$_2$-bpy)
Ru(bpy)$_2$(5,5'diCO$_2$Etbpy)
Ru(bpy)$_2$(4,4'diCO$_2$Etbpy)
where Et is ethyl, bpy is bipyridyl, dmbpy is dimethyl bipyridyl, MeIm is N-methyl imidazole, MeHIm is methyl imidazole, HIm is imidazole, phen is phenanthroline, mphen ismethyl phenantholine, dmphen is dimethyl phenanthroline, tmphen is tetramethyl phenanthroline, dmdpphen is dimethyl diphenyl phenanthroline, phphen is phenyl phenanthroline. In addition, it is understood that reduced or oxidized forms of these mediators may be used, either alone or in combination with each other.

Patents relating to particular mediators include U.S. Pat. Nos. 4,318,784, 4,526,661, 4,545,382, 4,711,245, 5,589,326, 5,846,702, 6,262,264, 6,352,824, 6,294,062, 4,942,127, 5,410,059, 5,378,628, 5,710,011, and 6,605,201 which are incorporated herein by reference.

The term "an opening having a rectilinear cross-section" as used in the specification and claims of this application is an opening having four straight sides. The reference to straight sides refers merely to sides that are not obviously curved when viewed, and does not imply a criticality of perfect linearity from the punching process. Non-limiting examples of rectilinear cross-section openings are trapezoids, parallelograms, squares and rectangles. The corners of the rectilinear openings are desirably rounded. Openings of this shape are preferred because the straight edges have less error in cutting, and the rounded corners are less prone to tearing.

The term "bound opening" refers to an opening which is surrounded by the material of the electrically resistive sheet, where there is no direct connection between the opening and the periphery of the resistive sheet. As described in greater detail below, a bound opening may have a single major open area, for example an opening having a rectilinear cross-section, or it may have more than one major open area connected by a generally narrower connecting portion.

The term "major open area" refers to a portion of a bound opening in which either the sample space or the connectors of an electrochemical cell will be formed.

The term "opposing electrodes" refers to electrodes disposed on different substrates used in the formation of the sample cell, such that they are disposed in different planes on the top and bottom (or on the two sides) of a cell, such that movement of charge carriers occurs in a direction generally perpendicular to the plane of the electrodes. "Opposing electrodes" are thus different from side-by-side electrodes in which an electrode pair is disposed on a common surface in a common plane, and the movement of charge carriers is generally parallel to the plane of both electrodes.

The term "punching" as used in the specification and claims of this application refers to the act of cutting through a sheet of material in a direction substantially perpendicular to the major surface. The term "substantially" in this case recognizes that there may be slight manufacturing deviations from absolutely perpendicular, but that these should be minimized to avoid top to bottom inconsistency in the dimensions of the openings created. Punching can be performed using a die cutting apparatus or other apparatus that physically cuts the layers into the desired shape. Laser cutting can also be employed where heat generation and/or evolution of volatiles is not a concern. Chemical etching through the materials might also be employed.

The term "unpatterned layer of conductive material" refers to a deposition of conductive material, for example by painting, sputtering, evaporation, screen printing, chemical vapor deposition, or electroless deposition onto the surface of a material without any defined patterning to define the electrode area. Patterning may be used for the contact pads or connector tracks, however, a wholly unpatterned layer may be employed for all of the conductive elements, and this is preferred since fewer manufacturing steps are involved. The unpatterned or wholly unpatterned layer is desirably a uniform coating, although random scratches, pits or other defects that may occur as a result of handling or manufacturing processes do not render a conductive material patterned.

Electrochemical Cells

Figure 1B:
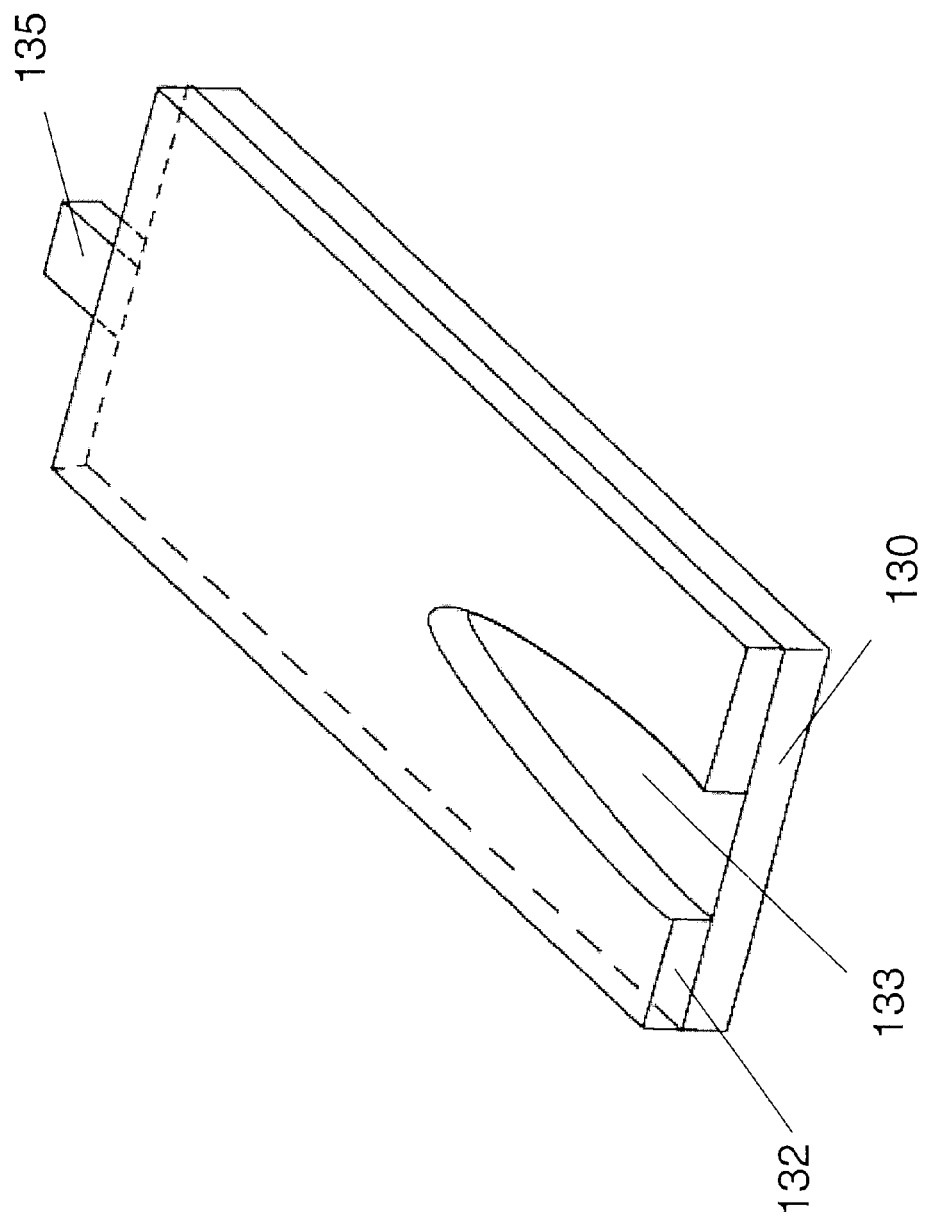

The method of the present invention is used to make electrochemical cells. FIG. 1A shows schematic representation of such a cell. The cell is formed from a bottom layer 130, a top layer 131, and a middle layer 132. The top and bottom layers are electrically conductive, at least on the surfaces facing the middle layer 132. In preferred embodiments, the top and bottom layers 130, 131 are an insulating substrate onto which a conductive layer has been coated. As more clearly shown in FIG. 1B in which the top layer 131 has been removed, the middle layer 132 has a notch 133 formed in one edge. The notch 133, and the top and bottom layers 130, 131 together define a space into which sample is received when the electrochemical cell is in use. The volume of this space is thus defined by the thickness of the middle layer 132 and the dimensions of the notch. The electrochemical cell also has contact areas 134 and 135 that are attachable to a meter to provide an electrical connection between the meter and the portion of the top and bottom layers 130, 131 that are exposed in the space for receiving a sample.

The middle layer 132 is an electrically resistive material which isolates the conductive layers, and prevents electrical conductivity between the electrically conductive top and bottom layers 130, 131, unless they are connected via a sample disposed in the space for receiving a sample. Non-limiting examples of suitable materials for use as this layer include polyimide, polyester, polyethylene terephthalate (PET), polycarbonate, glass, fiberglass or other nonconductive materials that provide the desired support. The middle layer 132 suitably has a thickness of 500 to 50 µm. Thicker materials can be used where larger sample volumes are acceptable. Thinner materials can be used, but may create difficulties in handling, and increased difficulty in drawing sample into the finished cell since this thickness determines one dimension of the sample space. In a preferred embodiment of the present invention, the sample space volume is less than 5 µl and more preferably less than 1 µl. In specific embodiments of the invention, the volume of the sample space is 500, 300, 200, 100 or 50 nl.

The conductive portion of top and bottom layers 130, 131 is selected consistent with the specific analyte that the electrochemical cell is intended to detect. Specific examples of suitable conductive electrode materials include gold, carbon, silver, palladium, and platinum. The conductive material used in the top and bottom layers 130, 131 may be the same or they may be different from one another. In a preferred embodiment of the present invention the conductive material is gold. The conductive portion of the top and bottom layers is suitably a thin coating on one surface of an insulating substrate sheet. Materials used for the middle layer 132 may be used as this substrate as well.

Depending on the analyte to be detected, the electrochemical cell may include a reagent composition disposed within the space for receiving a sample. In the case of an electrochemical cell for the detection of glucose, this reagent composition suitably comprises an enzyme effective to oxidize glucose, for example glucose oxidase, and a redox mediator, for example ferricyanide. Reagent compositions for this purpose are known in the art, for example from U.S. Pat. No. 4,711,245 to Higgins et al. and U.S. Pat. No. 5,437,999 to Diebold et al., which are incorporated herein by reference. A particular embodiment of the reagent comprises glucose oxidase and ferricyanide.

In addition to its electrochemical function, the reagent composition, when present, may assist in overcoming the hydrophobicity of the sample space, so that blood or other aqueous sample can be drawn into the space by the hydrophilicity of the reagent. Where a reagent is not used, surface treatment of the sample volume to reduce hydrophobicity and to facilitate sample introduction may be indicated, for example with Triton or other surfactants.

Figure 2:
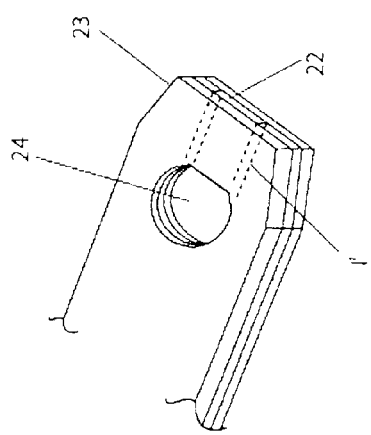
FIGS. 2A and B shows the sample receiving tip end and the sample space of a further embodiment of an electrochemical cell made in accordance with the invention.
Figure 2:
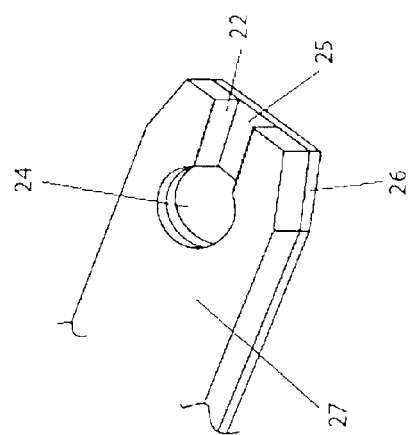

FIGS. 2A-B shows the sample receiving tip end and the sample space of a further embodiment of an electrochemical cell made in accordance with the invention. In FIG. 2A, the device is fully assembled. The sample space 22 extends from the tip 23 of the device to a hole 24. The length l of the sample chamber is on the order of 1 mm, for example from 1.5 mm to 0.5 mm, although longer lengths can be used to make sample spaces with larger volumes. FIG. 2B shows the tip region of FIG. 2A with the top layer removed. The conductive surface 25 of the bottom layer 26 is visible in the bottom of the sample space 22. The sample space 22 is defined on the bottom by the conductive surface 25 of sheet 26 and on the sides by the resistive sheet 27. The ends of the sample space are open at the end of the device and to the hole 24.

FIG. 3A shows a top view of a variation of the sample receiving tip region of FIG. 2A. In this case, at least the distal portion (i.e, the portion towards the tip end) of the hole 34 is shaped to be complementary to the shape of the tip end. The term "complementary" means that the profile of the front of the strip 36 is identical to the profile of the front of the hole 38, the former being displaced from the latter by movement in the direction of the length of the sample space or channel 22 This configuration is desirable to maintain a consistent volume for the sample space, and a consistent area of the electrodes even when the alignment of the sample space with the rest of the device is imperfect. (FIG. 3B). This configuration also allows multiple sample spaces in the tip of the device with the same benefits, as shown in FIGS. 3C and 3D.

Figure 4A:
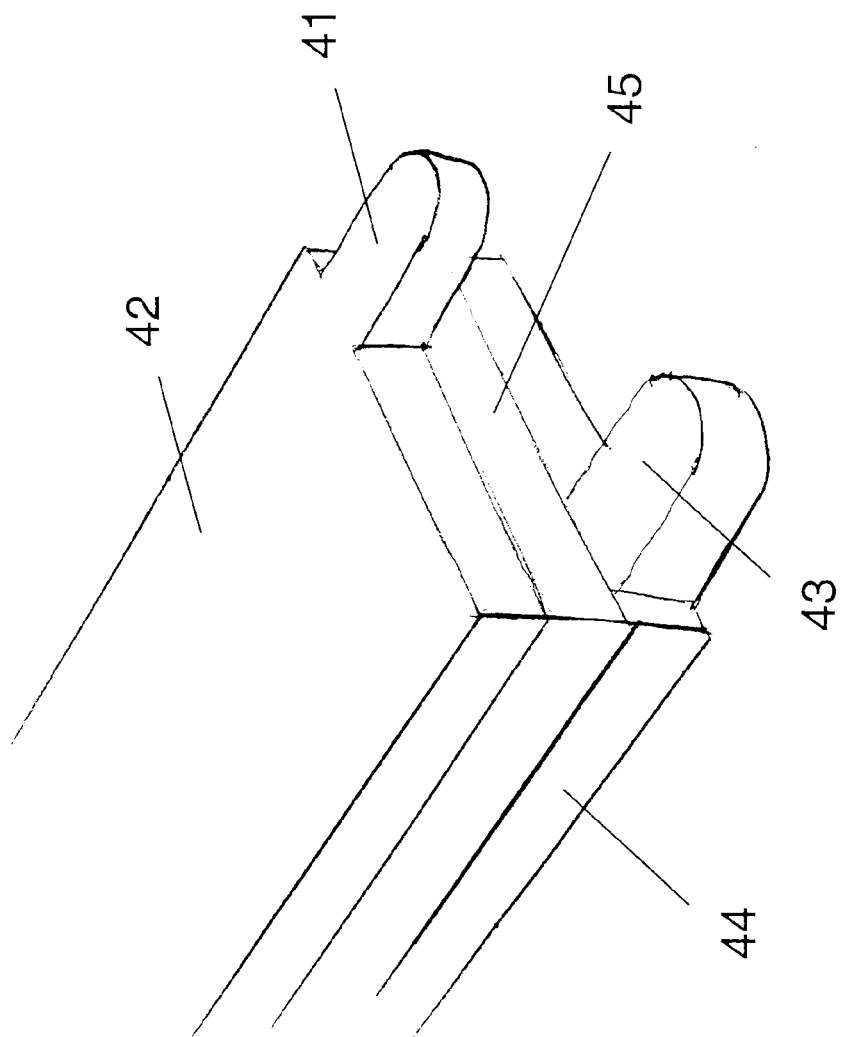
FIGS. 4A-C show different embodiments of the connector end of electrochemical cells made in accordance with the invention.
Figure 4B:
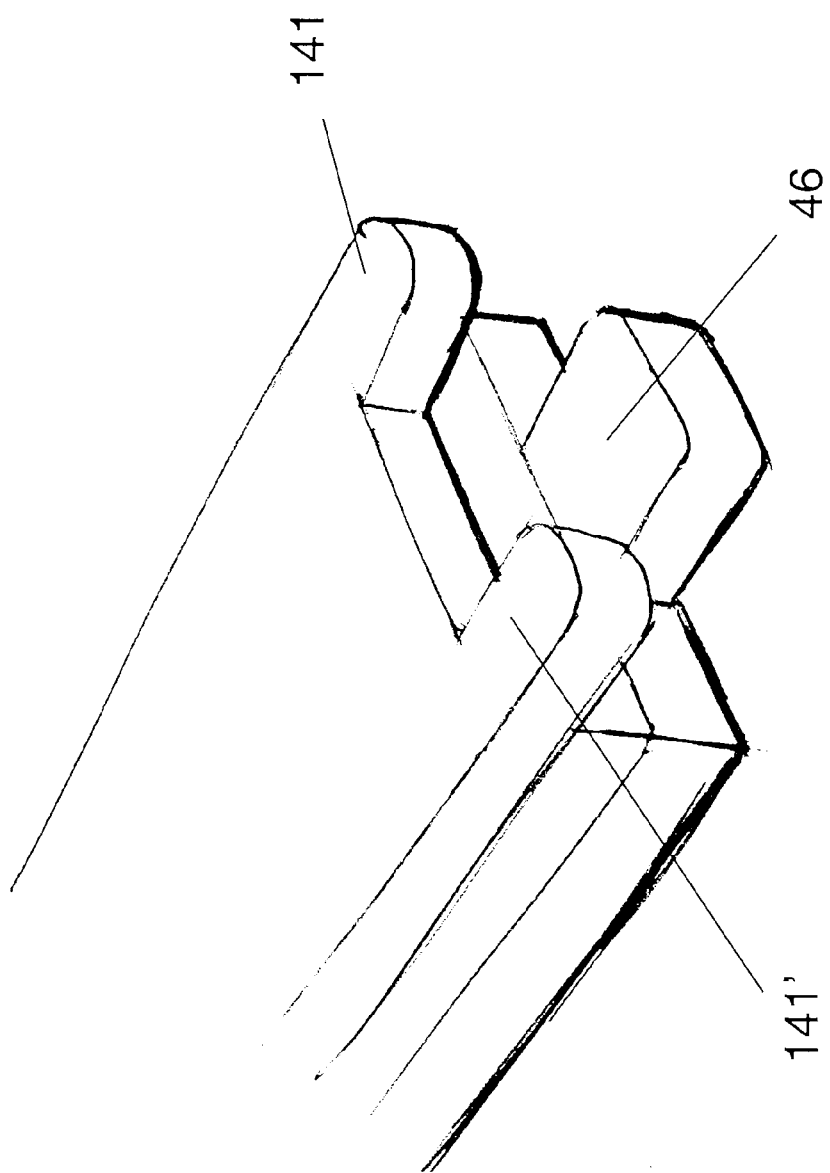
Figure 4C:
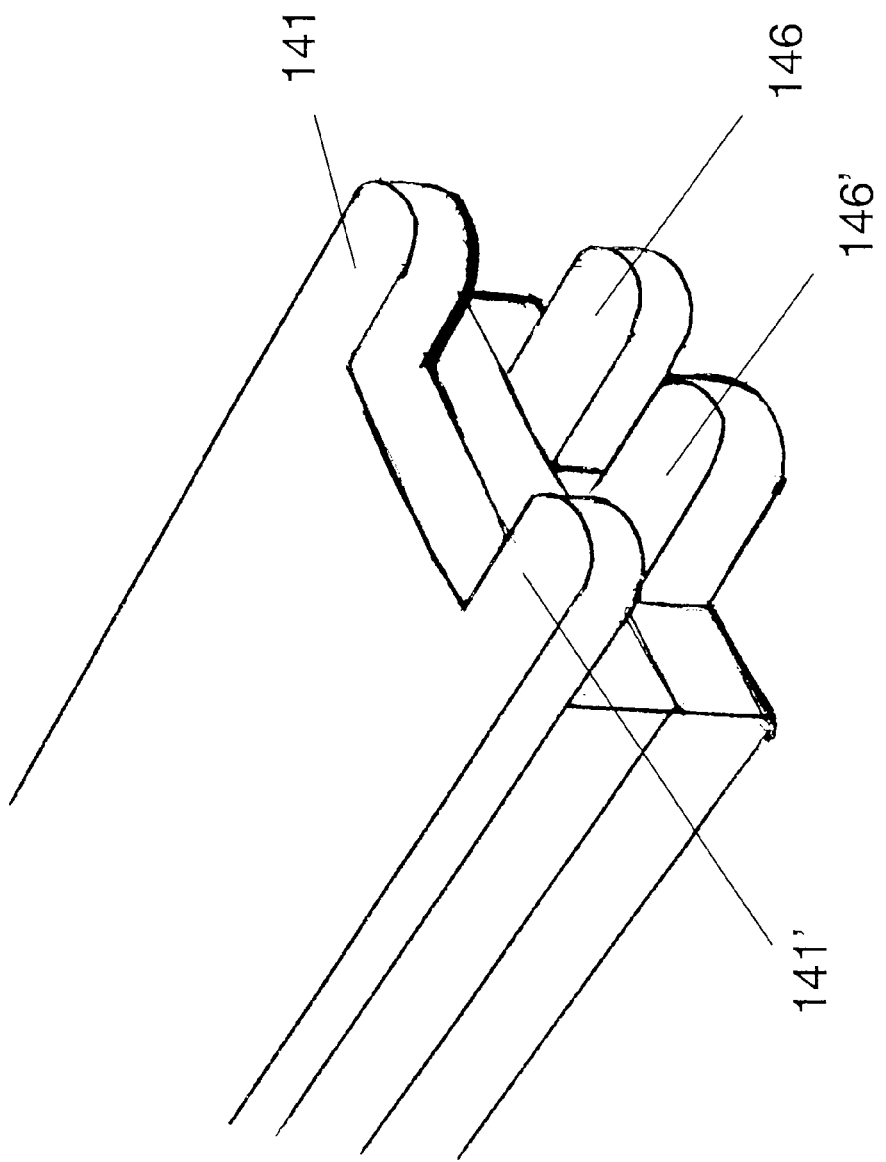

FIGS. 4A-C show different embodiments of the connector end of electrochemical cells made in accordance with the invention. In FIG. 4A, connector tab 41 extends from the end of the device as an extension of the first conductive layer 42 with the conductive surface facing downwards in the orientation shown. Connector tab 43 extends from the end of the device as an extension of the second conductive layer 44 with the conductive surface facing upwards in the orientation shown. Electrically resistive layer 45 is shown between the conductive layers 42, 44. FIG. 4B shows an alternative embodiment in which two peripherally located tabs, 141, 141' extend from the top conductive layer and one centrally located tab 46 extends from the bottom conductive layer. FIG. 4C shows a further alternative embodiment in which two peripherally located tabs, 141, 141' extend from the top conductive layer and two centrally located tabs 146, 146' extend from the bottom conductive layer.

Method of the Invention

In accordance with the method of the invention, an electrochemical cell as described above is constructed by punching one or more bound openings into an electrically resistive sheet thereby forming a punched electrically resistive sheet having at least one bound opening. Bound openings are preferred in the method of the invention because such openings have greater dimensional stability than a notch cut into the edge of a sheet, and therefore provides less manufacturing variation in the size of the space for receiving a sample. In an embodiment of the present invention the bound openings in the electrically resistive sheet are of "rectilinear cross-section."

The punched electrically resistive sheet is adhered to a first electrically conductive sheet thereby forming a combined sheet in which a conductive surface of the first electrically conductive sheet is visible through the first and second openings in the punched electrically resistive sheet. The specific material used to accomplish the adherence is not critical, although thick layers of adhesive that could contribute variation in the size of the space for receiving a sample are not desirable. A preferred example of an electrically resistive sheet coated with adhesive is one made with a pressure-sensitive acrylic adhesive such as ARCARE 7841 made by Adhesives Research. Other examples of commercially available adhesives applied to polyester substrates are made by 3M: 3M #444, 3M # 443 and 3M #1512. Selection of the adhesive product is driven, at least in part, by the desired height of the sample space which is defined by the substrate plus the adhesive coatings. The adhesive is suitably applied over the entire electrically resistive layer to form a uniform coating, as is available in commercial double sided "tapes." Heat sealing might also be used as could techniques such as ultrasonic welding.

The next step is punching a notching opening through the electrically resistive sheet and the first electrically conductive sheet of the combined sheet. The notching opening transversely intersects the first bound opening in the electrically resistive material, i.e., it cuts through two sides, preferably two opposed sides in a rectilinear first bound opening of the first bound opening, thereby transforming the first bound opening into a notch in the electrically resistive sheet. This results in the formation of a first electrode area that is defined by the notching punch of the combined sheet and by the notch in the electrically resistive sheet. In addition, a first electrical contact is formed by punching through the portion of the electrically conductive sheet visible through the second bound opening of the electrically resistive sheet to form a first electrical contact, thereby forming a punched combined sheet. In a preferred embodiment, a single punching step is used to form both the notching opening and the first electrical contact.

A second electrically conductive sheet is punched with a punch or punches to form an electrically conductive sheet having a notching opening corresponding to that of the punched combined sheet, thereby forming an opposite electrode sheet having a second electrode area and a second contact area in the second electrically conductive sheet. As used in the specification and claims of this application, an electrically conductive sheet having a notching opening corresponding to that of the punched combined sheet is one in which the opening in the resulting opposite electrode sheet will substantially align with the openings and notches of the punched combined sheet when the second electrically conductive sheet is adhered to the punched combined sheet. Indeed, for ease of manufacture, the same punch or punches (i.e., either the same physical unit, or one with identical dimensions) can be used to form the opposite electrode sheet as was/were used to form the punched combined sheet. The invention does not, however, exclude embodiments in which the dimensions of the opposite electrode sheet are intentionally made to be different so as to provide working and counter electrodes of different dimensions.

An optional step of adding a reagent may be performed. For ease of manufacturing the desired reagent may be added to the punched combined sheet, wherein the notch in the electrically resistive material serves as a reservoir for holding the added reagent. Alternatively the reagent may be added to first or second electrically conductive material or both either prior to or after being punched. In yet another embodiment no reagent is added during the production of the electrochemical cell. In such a case, if a reagent is desired it may be added directly to the sample within the electrochemical cell or prior to the sample's introduction to the cell.

If desired, different reagents may be applied on the two opposing electrodes. Because of the small separation of the electrodes, diffusion of the reagents is rapid when sample is present, but this approach allows two reactive reagents to be kept apart until sample is added. For example, if the presence of an enzyme inhibitor is being determined through loss of enzyme activity, it would be undesirable to have a single reagent containing enzyme and substrate since they could react during the deposition process. In particular, a phosphatase such as alkaline phosphate can be used to cleave a phosphate substrate to produce an electrochemically detectable product (such as p-aminophenol). This reaction can be inhibited by excess phosphate, arsenates and shellfish toxins, making it useful in a variety of analyte-specific devices. Separate reagent depositions might also be used to separate an enzyme from a buffering agent, so that the enzyme was only at a correct pH for reaction after sample addition and combination of the reagents.

After the formation of the corresponding opening and the second electrical contact in the second electrically conductive sheet, the resulting opposite electrode sheet is adhered to the electrically resistive sheet portion of the punched combined sheet with an electrically conductive surface facing the electrically resistive sheet. The opposite electrode sheet is adhered such that the punched opening in the opposite electrode sheet corresponding to the notching opening in the combined sheet is aligned with the notching opening in the combined sheet, and the second contact area is aligned with the second bound opening of the combined sheet. This results in the formation of an electrochemical sheet in which a second electrode area is defined on the opposite electrode sheet by the notch in the electrically resistive sheet and the dimensions of the punch of the second electrically conductive sheet.

Finally, the electrochemical sheet is cleaved to form a spent electrochemical sheet from the surrounding material and a free electrochemical cell having a space for receiving a sample defined by the first and second electrodes and the notch in the electrically resistive material, and first and second contact areas in electrically-conductive contact with the first and second electrodes for connection of said first and second electrodes with a meter. This step can be performed on one cell at a time, on one sheet of cells at a time, or on multiple cells or sheets in a combined operation.

It will be appreciated that multiple cells can be formed from each sheet of material by formation of multiple sets of punches adjacent to one another. It will also be appreciated that multiple cells can be formed immediately adjacent to each other, so that no excess material is left between them when they are cleaved. Multiple strips can also be formed from a single sheet in a "nose to tail" or "nose to nose and tail to tail" arrangement such that punching of a single bound opening forms the nose of one strip and the tail of the next strip at once, or nose and nose, or tail and tail.

In an embodiment of the present invention a sample is drawn into the electrochemical cell by the hydrophilic nature of the dried, soluble reagent. To prevent an air lock that would inhibit filling, a vent is often required for venting of gases from the cell as the sample is drawn into the cell. For such a case the punched combined sheet may further comprise a vent opening punched through the electrically resistive sheet and the first electrically conductive sheet, wherein the vent opening is aligned with the notch in the electrically resistive sheet to form a passageway for air that connects to the interior of the space for receiving a sample.

Alternatively the vent opening may be punched through the second electrically conductive sheet of the combined sheet, wherein the vent opening is aligned in the assembled cell with the notch in the electrically resistive sheet to form a passageway for air that connects to the interior of the space for receiving a sample. In yet another embodiment both vent openings may be punched. A sample may be drawn into the sample area through a vent or through the opening between the electrically conductive sheets.

Figure 3:
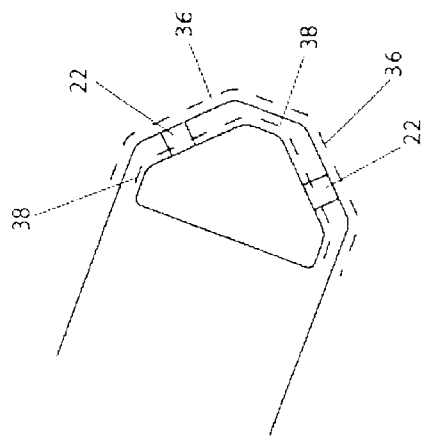
FIG. 3A-D show top views of embodiment of a sample receiving tip end.
Figure 3:
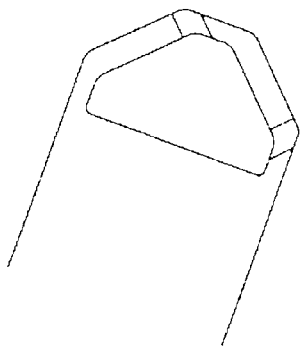
Figure 3:
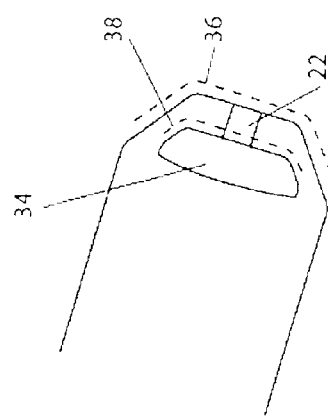
Figure 3:
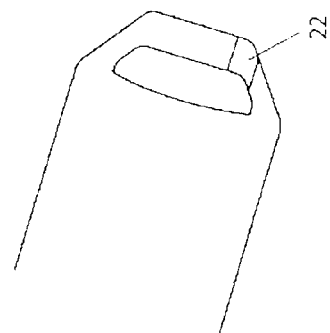

In a preferred embodiment of the invention as illustrated in FIGS. 2A, 2B and 3, the vent hole 24, 34 is formed such that it transversely cuts through the notch and thereby defines the proximal end (i.e,. the inward end) of the sample space 22. In this case, it will be appreciated that the proximal "vent hole" may actually act as the point of sample introduction with the distal opening serving the function of a vent. A vent hole of this type may be formed through the entire device (i.e, through the first conductive sheet, the electrically resistive sheet and the second conductive sheet), or through only one of the conductive sheets and the electrically resistive sheet.

Figure 5:
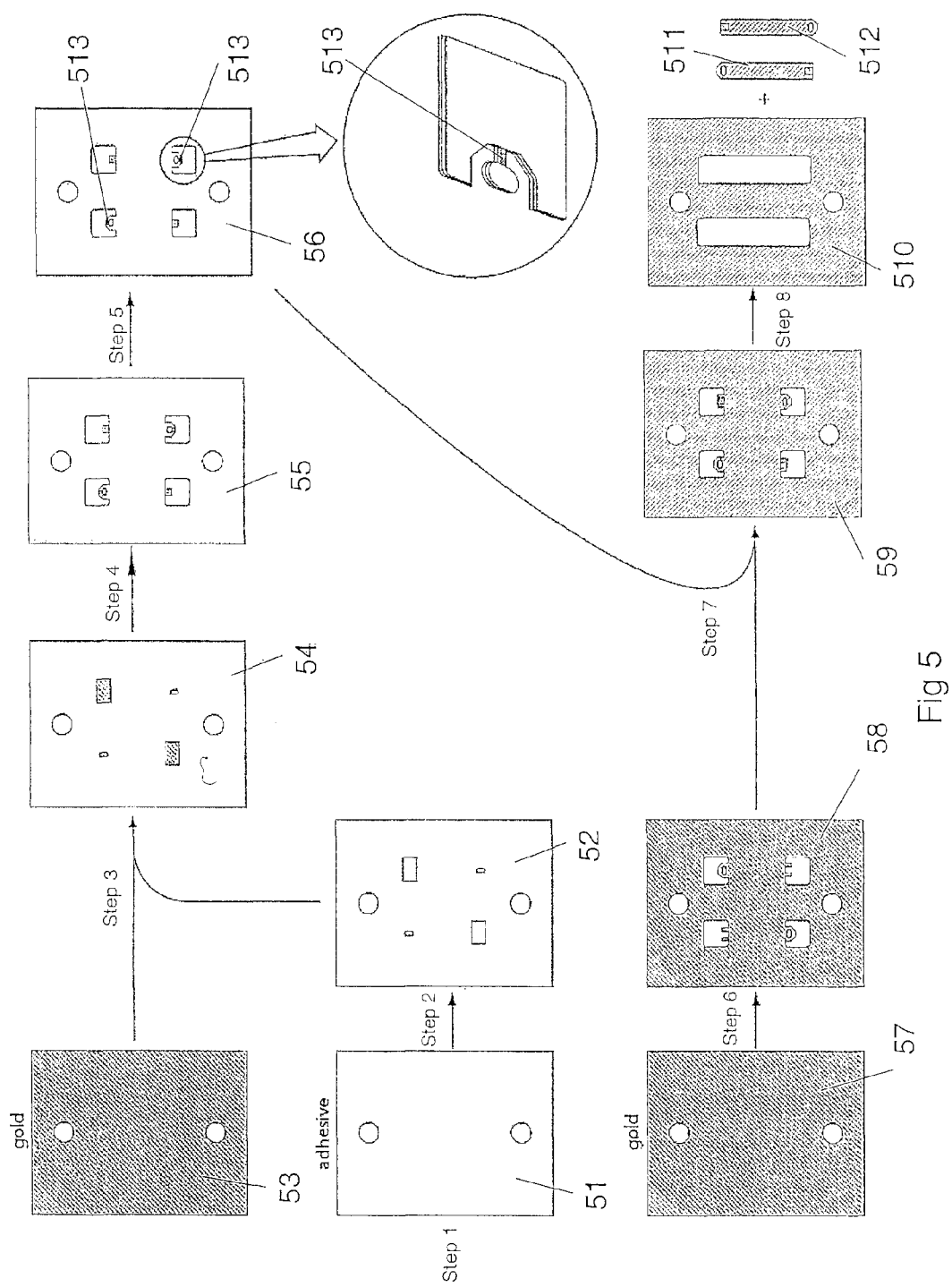
FIG. 5 shows a schematic of the steps of the invention.

A specific embodiment of the method of the invention is shown in FIG. 5. The following steps illustrate a process for the production of two electrochemical cells. It will be appreciated, however, that the process may be altered to produce one cell at a time, or to make more than two electrochemical cells using the same steps in a mass production operation.

Step One: An electrically resistive sheet is provided. The electrically resistive sheet 51 is coated with an adhesive on both major surfaces thereof.

Figure 6A:
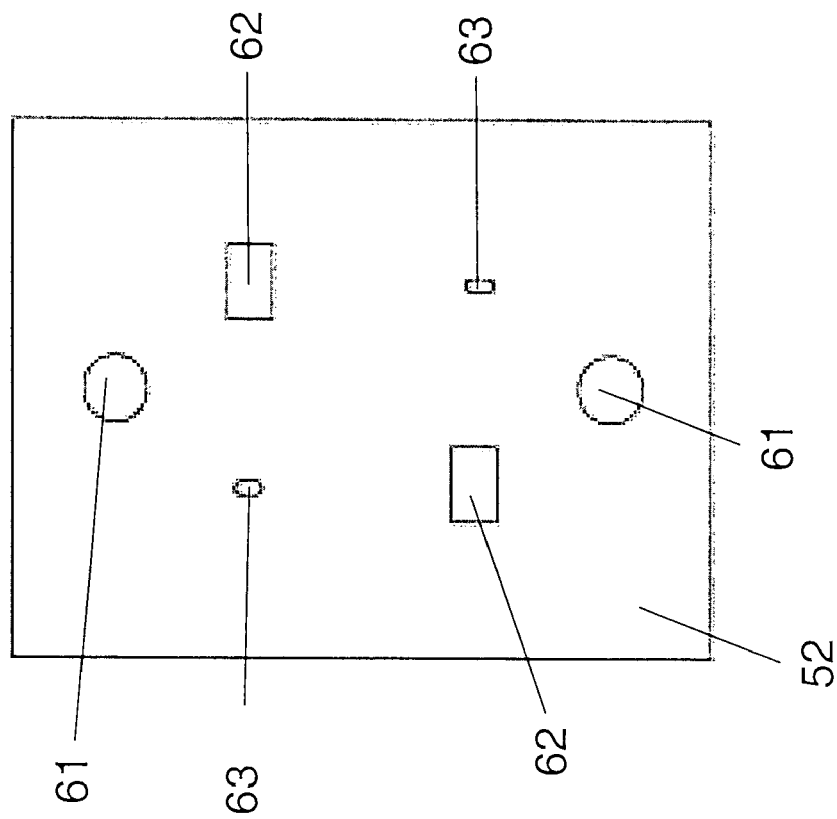
FIGS. 6A and B show embodiments of electrically resistive sheets having bound openings.
Figure 6B:
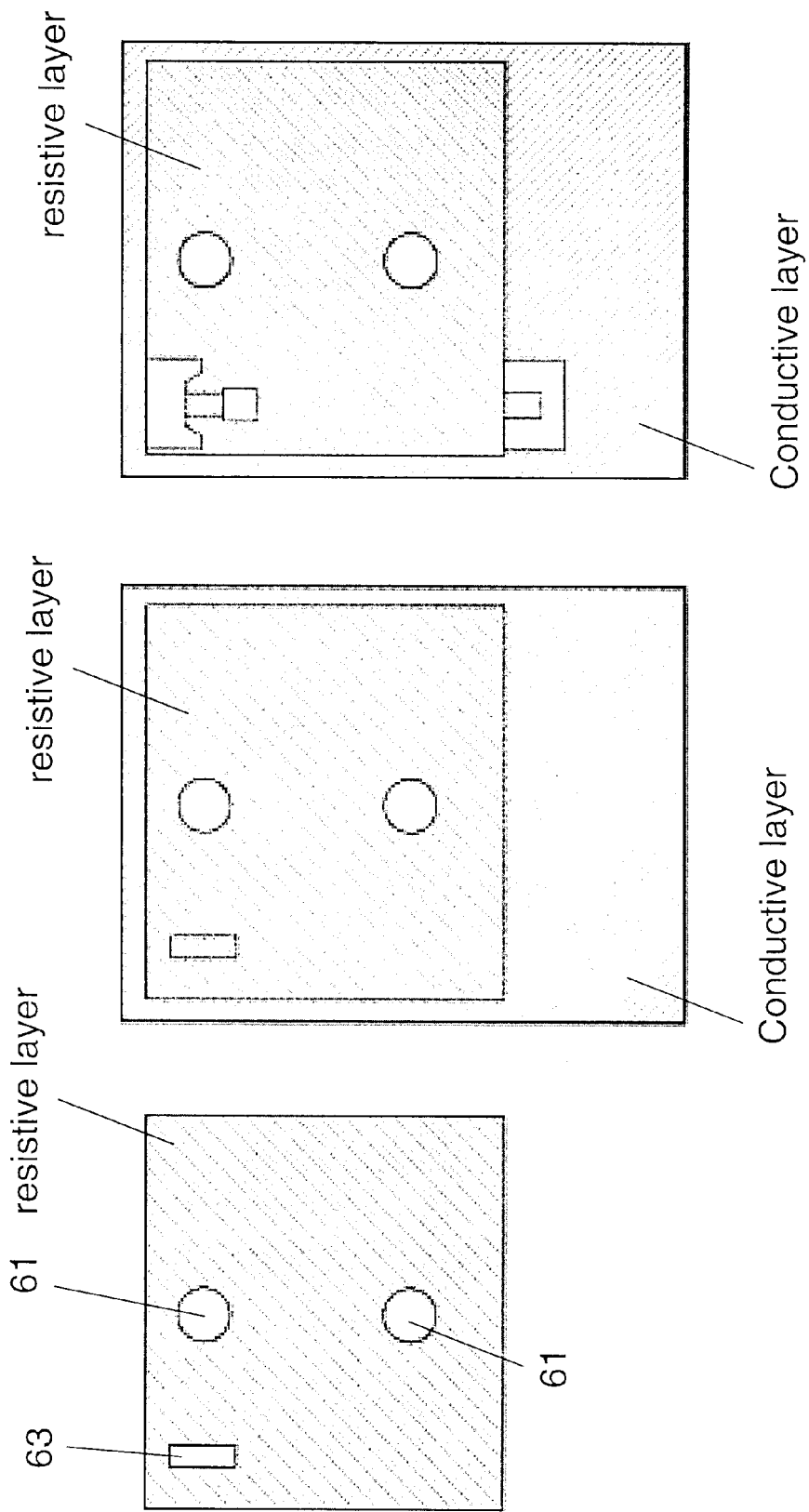

Step Two: As shown in detail in FIG. 6A, two registration holes 61 are provided to the electrically resistive sheet 51 from step one for manufacturing alignment and do not become part of the final device. The electrically resistive sheet 51 is placed into a die assembly (not shown) wherein the die assembly aligns the electrically-resistive sheet via the two registration holes. The electrically resistive sheet 51 is then punched thereby forming a punched electrically-resistive sheet 52 with two large and two small openings through the sheet. The large openings 62 are the openings through which the electrical connectors will be formed. The small openings 63 are the openings across which the notching opening and the vent opening will be made to define the sample space. FIG. 6B shows an alternative construction in which the conductive layer extends beyond the edges of the resistive layer, and the connector is formed in this extension. Thus, only one bound opening, which is involved in the formation of the sample space, is needed.

Step Three: The punched electrically resistive sheet 52 is then adhered to a first electrically conductive sheet 53 thereby forming a combined sheet 54. The electrically conductive sheet has at least one surface coated with a conductor, for example gold, which faces the punched electrically resistive sheet 52, and includes two registration holes in alignment with the registration holes of the electrically resistive sheet 52. Once the combined sheet 54 is formed, the conductive surface of the first electrically conductive sheet 53 is visible through the openings in the punched electrically resistive sheet 52.

Figure 7:
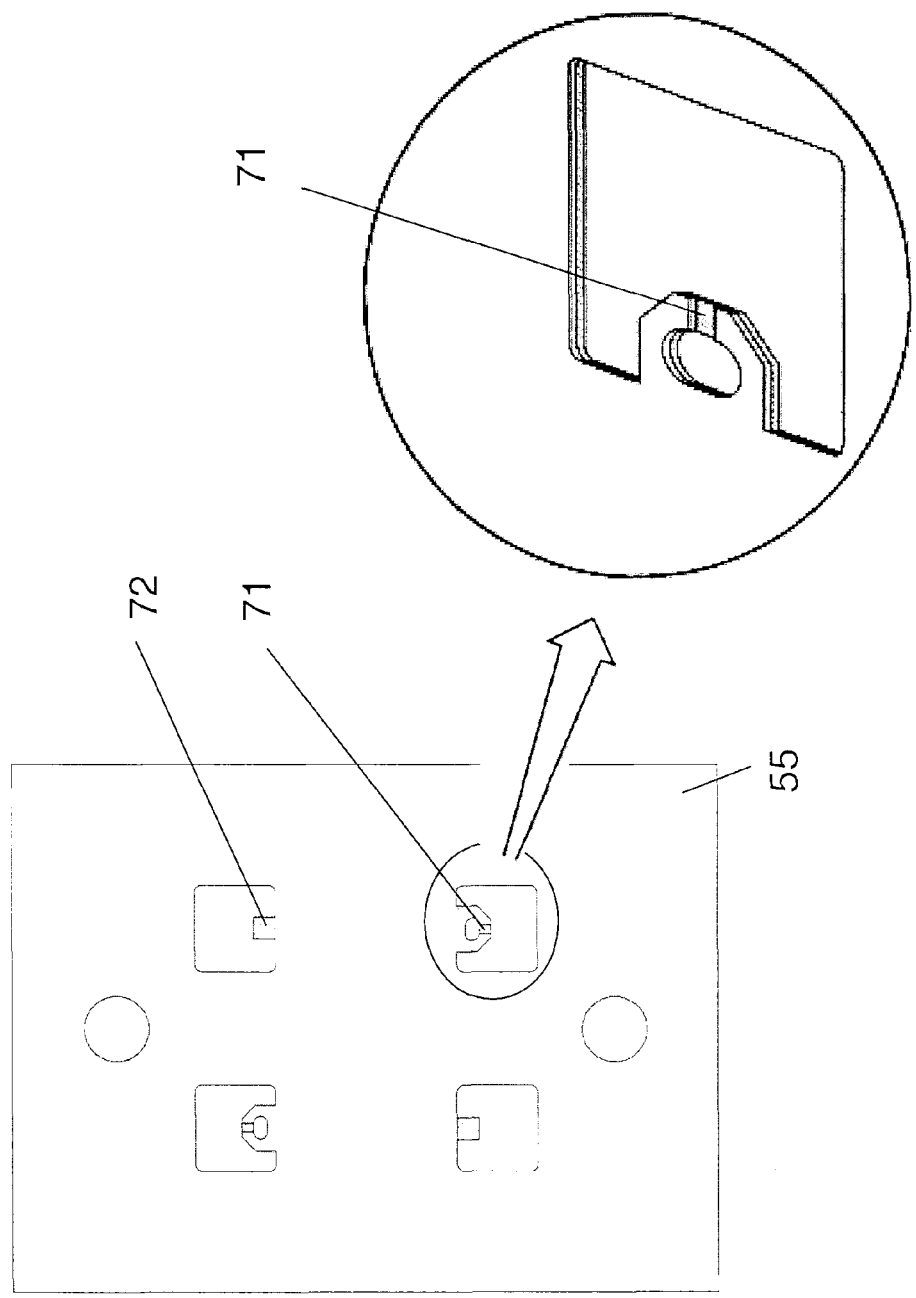
FIG. 7 shows a detailed view of a combined punched sheet formed in the method of the invention.

Step Four: The combined sheet 54 is punched, thereby forming a punched combined sheet 55. FIG. 7 shows this punched combined sheet 55 in greater detail. The punched combined sheet 55 is cut such that both the proximal and distal ends of the rectangular opening 63 are cut off, leaving the start of a generally rectangular/square sample space 71. The punch of step four also defines a first electrical connector 72 through which the electrode formed from the first electrically conductive sheet may be electrically connected with a measuring device.

Step Five: A reagent 513 is added to the punched combined sheet 55 over the sample space 71, thereby forming a reagent sheet 56. For a glucose sensor, the reagent that is added to the punched combined sheet 55 suitably comprises glucose oxidase and a redox mediator comprising ferricyanide. Preferably, the mediator is added in a liquid carrier that has a volume sufficient to fill at least 50%, and more preferably a greater portion of the sample space. This results in a coating of the mediator higher on the walls of the sample space, and therefore closer to the second electrode. This decreases the time for mediator to reach the second electrode during use, and thus improves the response time of the device.

Figure 8:
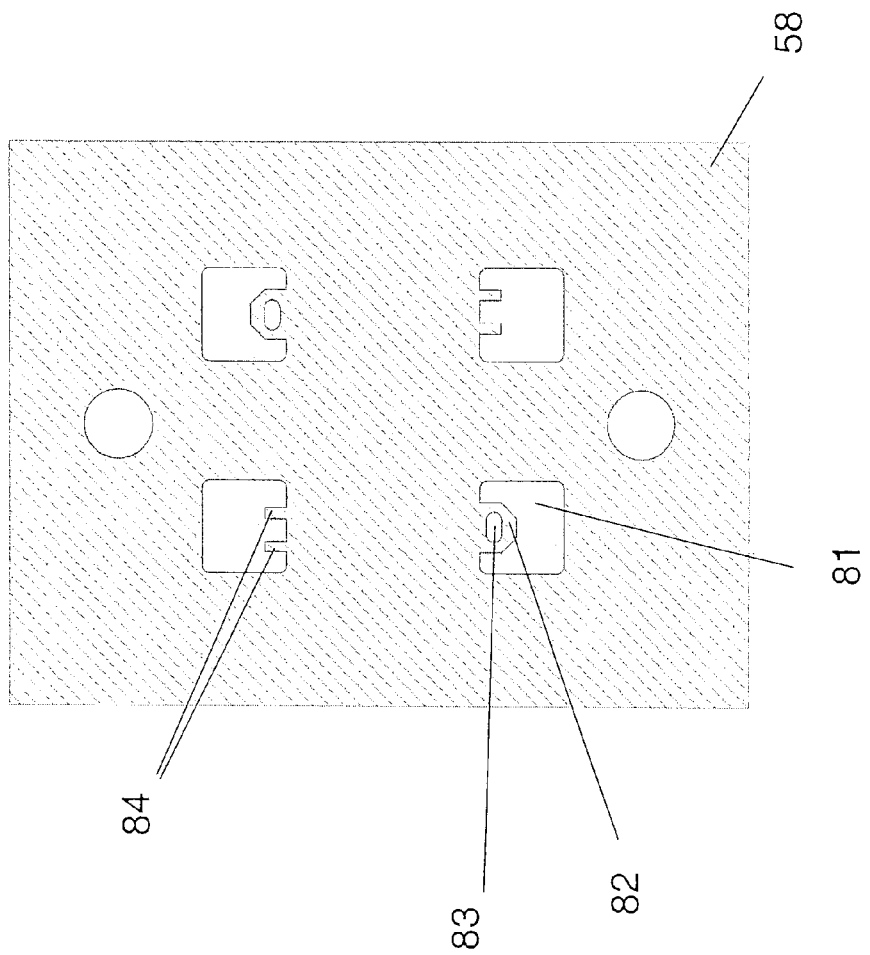
FIG. 8 shows a detailed view of a punched second conductive sheet formed in the method of the invention.

Step Six: Two registration holes are provided to a second sheet of an electrically conductive material 57. The two registration holes are for manufacturing alignment and do not become part of the final device. Electrically conductive sheet 57 is placed into a die assembly (not shown) and is punched, thereby forming an opposite electrode sheet 58. The punch used defines the top electrode for the sample space. Thus, as shown in FIG. 8, punched opening 81 defines a device tip 82 and a vent hole 83 having the same shape as those in the punched combined sheet 55. The punch also defines a second connector area 84, for connecting the electrode formed from the second sheet of electrically conductive material. The punch forming the second connector area 84 need not be the same as the punch forming connector area 72. What is desired is the ultimate of two sets of accessible contacts that do not make electrical contact one with another.

The second electrically conductive sheet 57 is suitably of the same material and construction of the first electrically conductive sheet 53, although it may be made of a different material, or include a label.

Step Seven: Opposite electrode sheet 58 is adhered to reagent sheet 56 from step five thereby forming an electrochemical sheet 59, wherein the registration holes of the opposite electrode sheet align with the registration holes of the reagent sheet. The conductive portion of opposite electrode sheet 58 is in contact with the electrically resistive sheet of the reagent sheet 6. This step results in the definition of the sample space, bounded by the two electrically conductive sheets on the top and bottom, and the electrically resistive sheet on the sides, and having openings at each end.

Step Eight: Electrochemical sheet 59 from step seven is cleaved thereby forming a spent electrochemical sheet 510 and two free electrochemical cells 511 and 512. It may be appreciated how the steps of this embodiment may be altered to result in a process that produces more than or less than two electrochemical cells.

Figure 9:
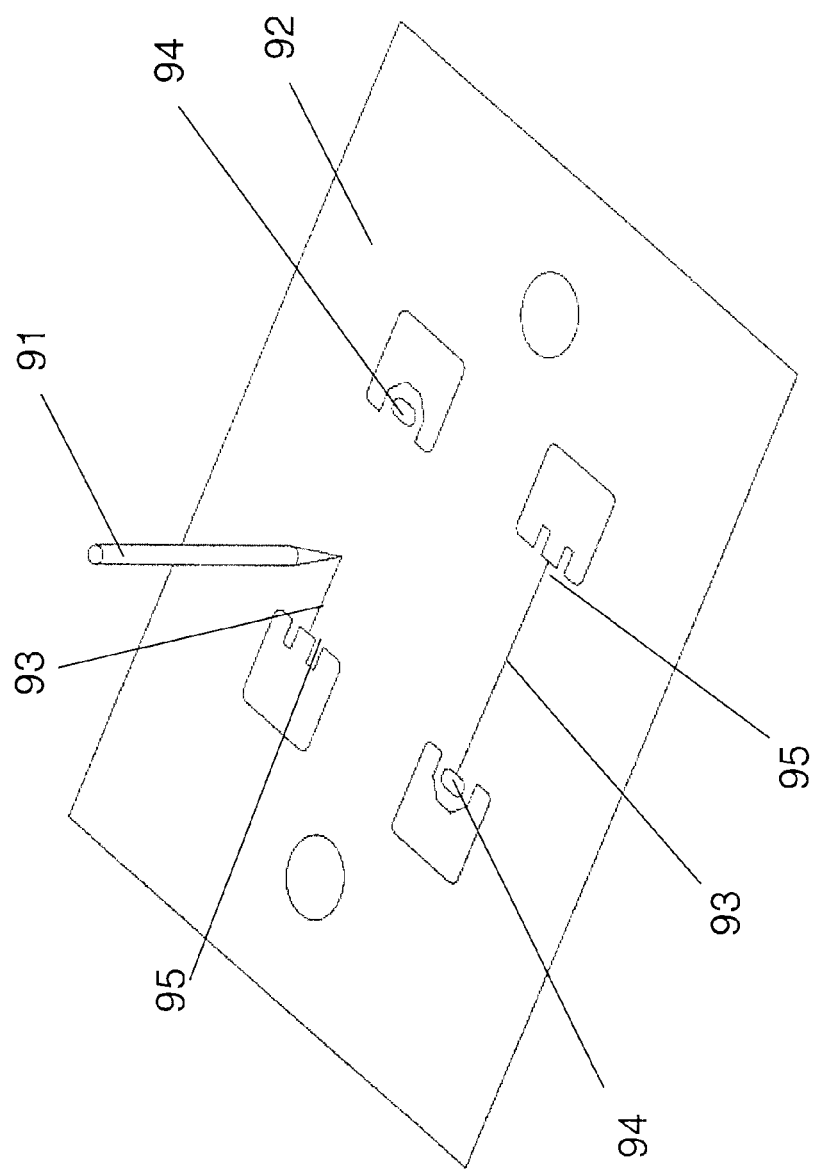
FIG. 9 shows a detailed view of a punched combined sheet useful in the method of the invention.

FIG. 9 shows a mechanism for dividing the portion of the conductive coating that does not form the electrode surface within the sample space to form two legs. A stylus 91 is dragged along the conductive surface 92 of the gold 58 to form a non-conductive line or gap 93 which divides the conductive surface from the vent hole 94 to the end of the strip at the connectors 95. This non-conductive line or gap 93 can be formed after defining the connectors and vent hole by punching, or before this, using the registration holes as a guide to ensure that scribed line is properly positioned. In the latter case, the scribe line may extend into the region that will be removed by puching. The non-conductive line for the first sheet must be formed before the electrically resistive sheet is adhered to the first conductive sheet (Step 3). Other methods for forming the non-conductive line or gap 93 besides simply dragging a stylus over the surface include the use of cutting wheels which may pass through the entire conductive layer, laser ablation and chemical etching.

Figure 10:
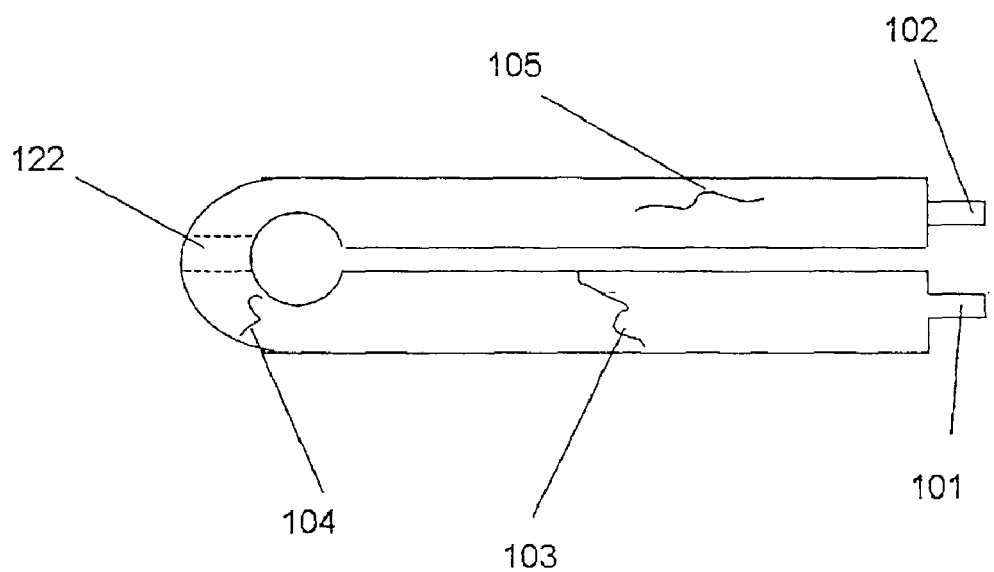
FIG. 10 shows a view of a split electrode formed using the method of the invention.

When this format is used to punch one or both of the conductive sheets, the result is a cell which can be readily tested for electrical continuity as part of a quality control procedure as illustrated in FIG. 10. FIG. 10 shows just the electrode layer of a cell if punching patterns and a scribed line as shown in FIG. 9 are used. The location of the sample space 122 is shown in dashed lines. If the electrical connection (for example via a conductivity measurement) is assessed between connectors 101 and 102, a good connection will be determined provided that there is no damages to the conductive sheet that extends all the way across either leg or the loop portion of electrode layer. For example, a scratch 103 or 104 would be detected as a fail, while a scratch such as 105 would not. Since connection between the electrode portion over the sample space 122 and either one of the connectors 101 or 102 is sufficient for a valid test result, this provides an easily achieved, non-destructive form of quality control which is actually more rigorous than the requirements of the operative device. The two intermediate connector tabs could also be formed by scribing, as shown in FIG. 9 intermediate along the length of this surface, without requiring a cut to configure the tabs.

Figure 11:
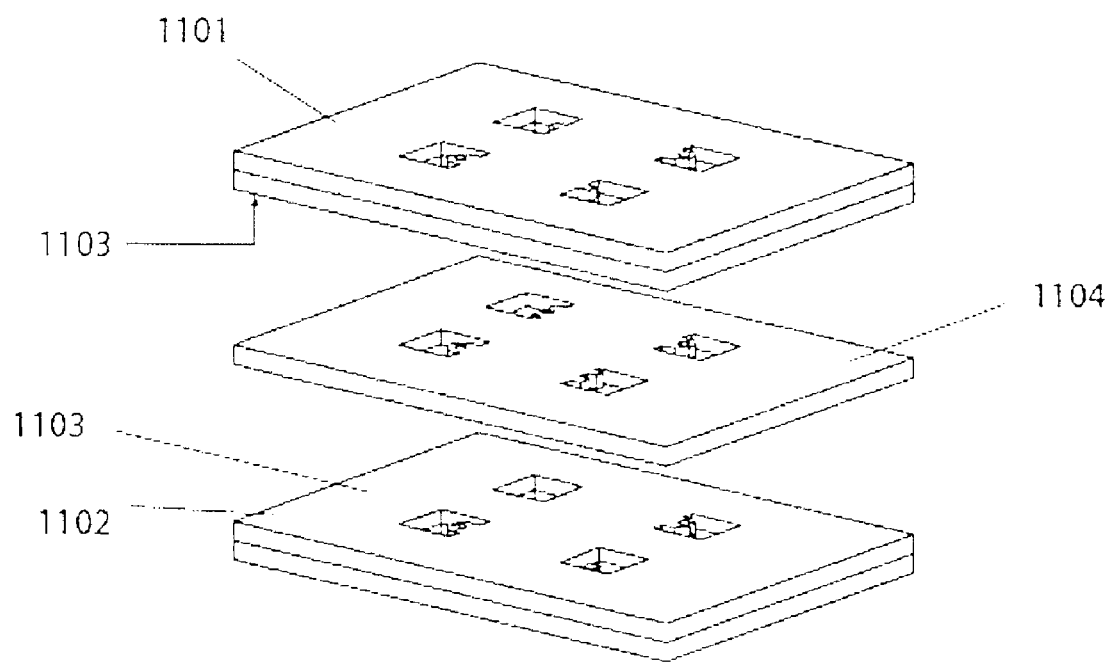
FIG. 11 illustrates the formation of a multi-test device using the method of the invention.
Figure 12A:
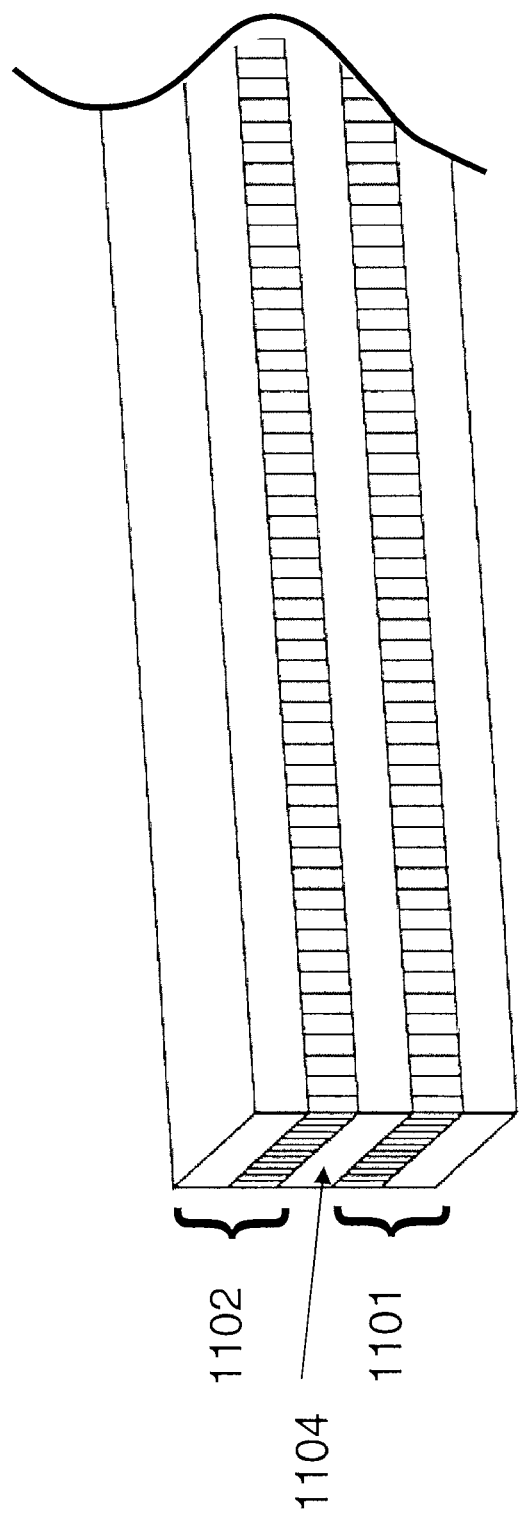
FIGS. 12A and B show cross sections through a multi-test device formed as in FIG. 11.
Figure 12B:
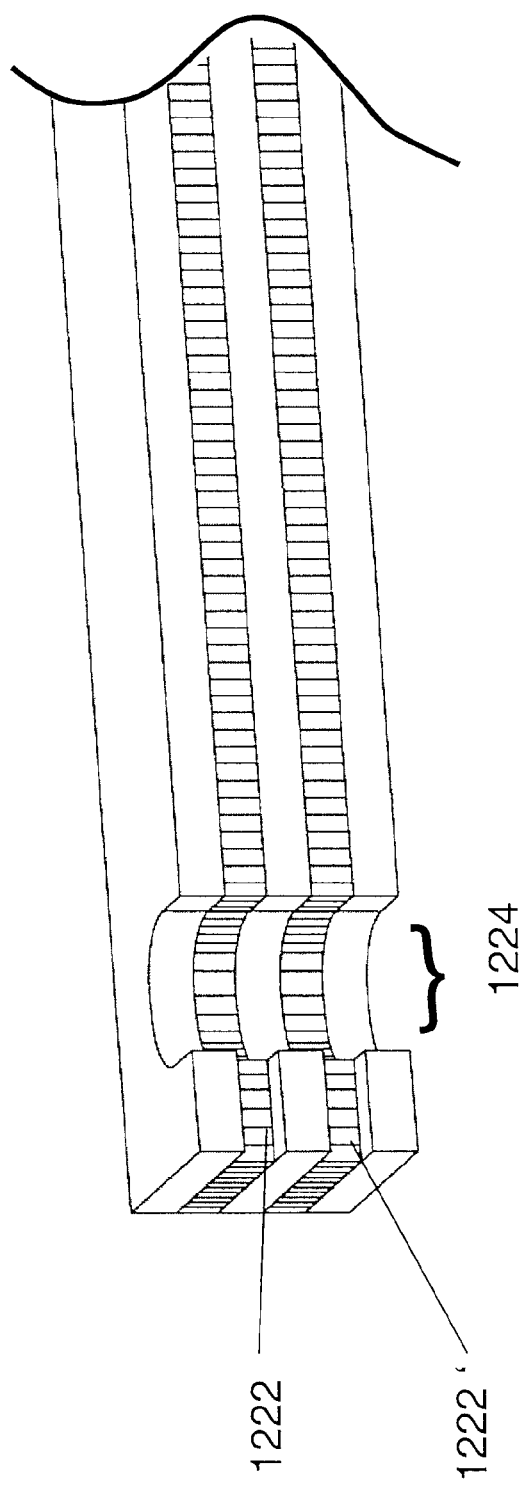

The method of the invention can also be used to make multi-test cell device. FIG. 11 illustrates a first method for accomplishing this result, in which two test cells are stacked one on top of the other. In this method, two punched combined sheets 1101 and 1102 are formed. as described above. Reagent is added to each punched combined sheet 1101, 1102 consistent with the analyte to be tested. The reagents added to sheets 1101 and 1102 may be the same or they may be different to provide for simultaneous testing of two analytes. Punched combined sheets 1101 and 1102 each have an adhesive inner surface 1103, 1103' and are adhered via this surface to an intermediate punched sheet 1104 formed from an electrically insulating material coated on both sides with a conductive layer. After cleaving the cell from the sheet, the result is a test device that has two stacked test cells. FIG. 12A shows a cross section through the resulting multi-cell device at a point remote from the sample space and vent hole. FIG. 12B shows a cross section through the resulting multi-cell device as a point intersecting the sample spaces 1222, 1222' and vent hole 1224. In each figure, the conductive surfaces are reflected by a wavy line. Because of the small size of the test cells, and the proximity of the openings, sample can be easily introduced into both cells concurrently.

Figure 13:
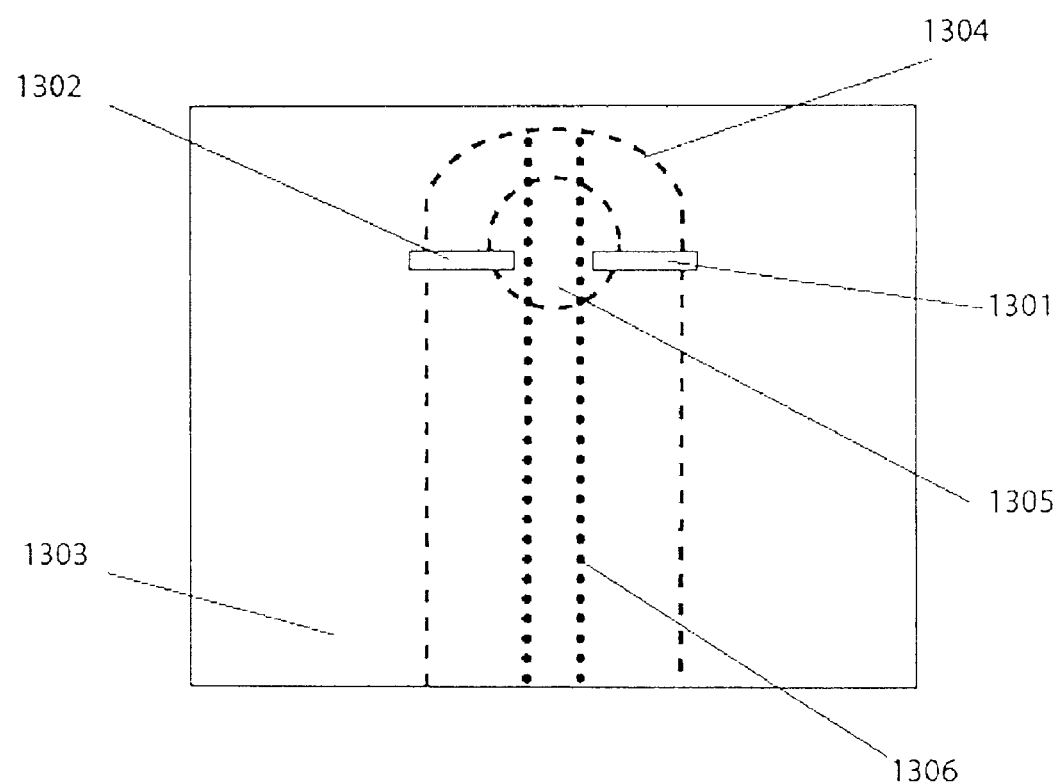
FIG. 13 illustrates the formation of another embodiment of a multi-test device using the method of the invention.

FIG. 13 illustrates an alternative embodiment of a method for making a multi-test cell device. In this embodiment, two or more adjacent sample spaces are formed. As depicted in FIG. 13, two openings are formed in place of the single first bound opening used to define the sample space in the embodiments described above. In the specific embodiment shown FIG. 13 A, two co-linear openings 1301, 1302 perpendicular to the long axis of the device are formed in the electrically resistive sheet. When the combined strip is punched along the dashed lines to form the device nose 1304 and vent hole 1305, the ends of both openings are cleaved, creating two sample spaces. In this configuration, the sample spaces are suitably filled from the vent hole. A cut or scribe along the dotted line 1306 is made in the electrically conductive sheet prior to assembly to provide electrical isolation for the two sample spaces. It will be appreciated that the same result could be achieved with one elongated opening that combined openings 1301 and 1302, and extended across the vent hole area between. Further, it will be appreciated that the relative specific positions of the openings formed in this embodiment are not critical, and that they need not be co-linear (e.g. FIG. 3C) provided that isolated electrical connections can be made to each sample space.

In a further embodiment of the method of the invention, multi-test devices can be made using a combination of the methods shown in FIGS. 11 and 12 with the method illustrated in FIG. 13. In this embodiment, the resulting device may have one or more cells in each stacked level.

In yet a further embodiment of the invention of the cell of FIG. 13, by displacing the openings 1301, 1302, and providing separate vent holes, two sample spaces can be formed in such a way that only one space is fillable from the outside edge, and the other only from the inside edge. In the absence of cut 1306, it does not matter which of the sample spaces was filled. This creates greater user convenience, since the sample collection point (the manner in which the strip is used) does not impact the result. Filling of both spaces can be distinguished from filling of only one based on determinations of effective electrode area, for example as described in US Patent Publication US 2005-0069892 A1 and U.S. patent application Ser. No. 10/907,813 filed Apr. 15, 2005, which are incorporated herein by reference.

Figure 14:
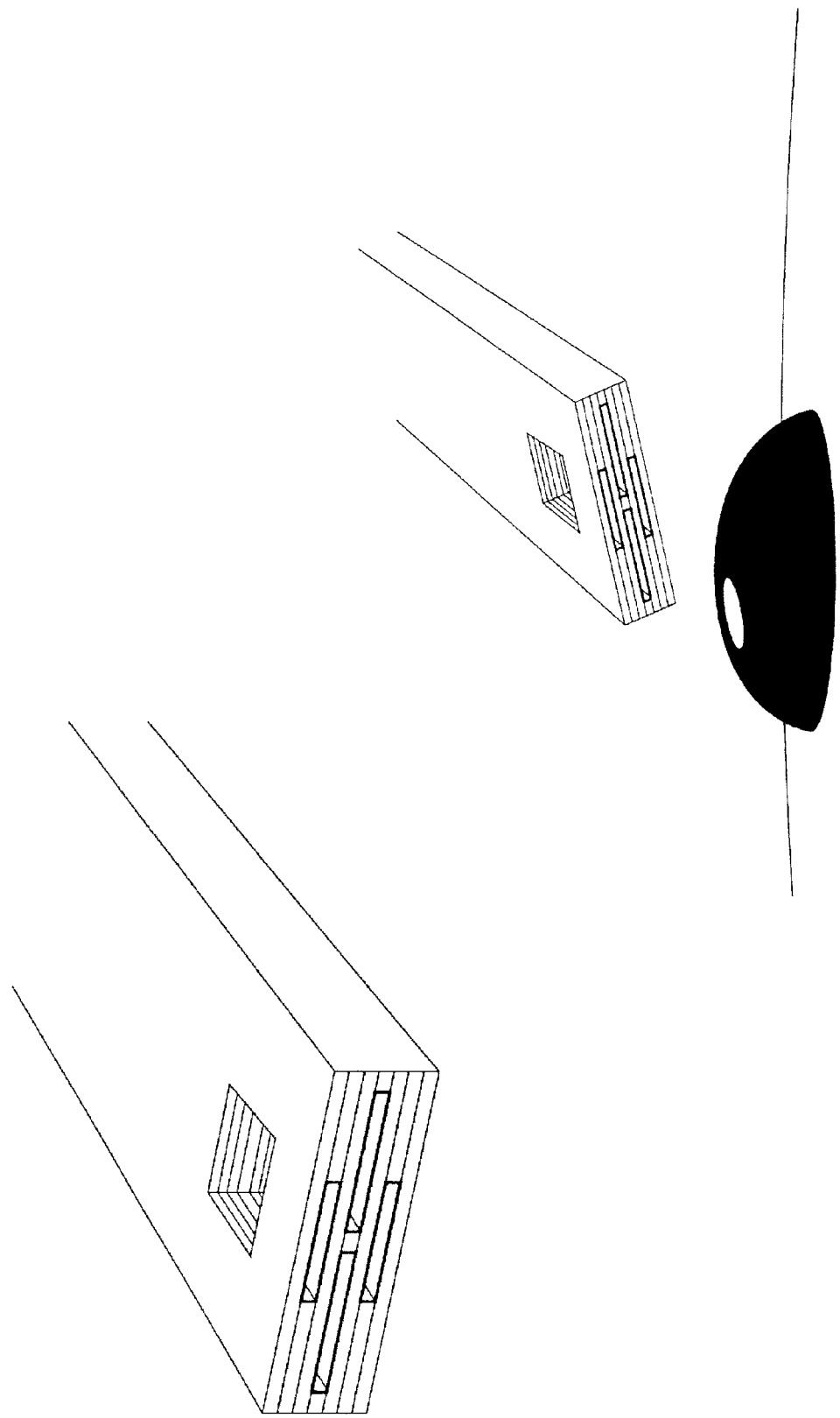
FIG. 14 shows another multi-cell test device.
Figure 15:
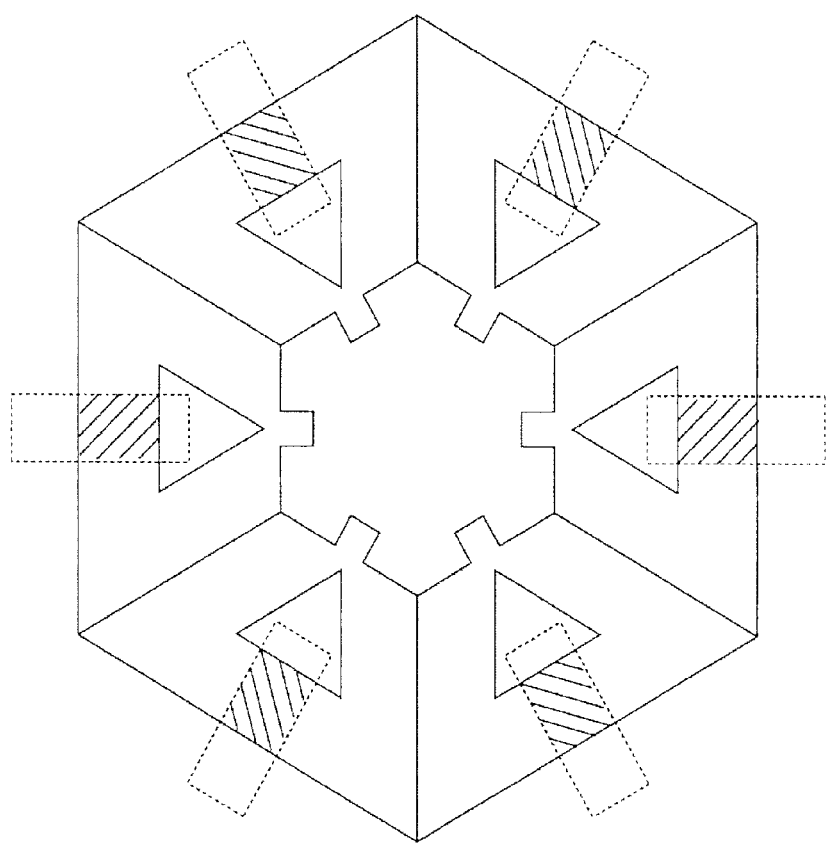
FIG. 15 shows another multi-cell test device.

FIGS. 14 and 15 show two other embodiments of multi-cell test devices. In FIG. 14, four sample spaces 1401 are formed, all of which are accessed via a common surface. Since filling (or partial filling) of any or all of these is sufficient to obtain a measurement, this configuration reduces the need to align a particular portion of the device tip with a blood/fluid droplet 1402. In FIG. 15, six sample spaces 1501 are aligned in a ring around a hexagonal multi-strip and extend from the outside of the ring to vent spaces 1502. The devices are separated by scribe lines 15-3 and have connector tabs 1504 directed to the center axis. In FIG. 15, only one conductive layer and the spacer layer are shown. A top layer with a conductive surface would complete the device with the other electrode and its associated connector tab(s).

Thus, it can be seen that the method of the invention provides flexibility in the formation of electrochemical test cells that include multiple sample spaces. These sample spaces may be coplanar, in which case they can be arranged in parallel, in a nose-to-tail arrangement, like the spokes of a wheel, in a wheel or in any other desired configuration. The sample spaces may also occupy multiple planes.

What is claimed is:

1. A method of manufacturing an electrochemical cell, wherein the electrochemical cell comprises opposing first and second electrodes separated by an electrically resistive sheet, wherein the method comprises the steps of:
   (a) forming a first bound opening in an electrically resistive sheet thereby forming a punched electrically resistive sheet;
   (b) adhering the punched electrically resistive sheet to a first electrically conductive sheet thereby forming a combined sheet, wherein a first portion of a conductive surface of the first electrically conductive sheet is exposed through the first bound opening, and a second portion of the conductive surface of the electrically conductive sheet is exposed either through a second bound opening in the electrically resistive sheet or as an extension beyond an edge of the electrically resistive sheet;
   (c) punching a notching opening through the electrically resistive sheet and the first electrically conductive sheet of the combined sheet, wherein the notching opening intersects the first bound opening in the electrically resistive sheet thereby transforming the first bound opening into a notch in the electrically resistive sheet, and punching a first contact area punch through the second exposed portion of the electrically conductive sheet visible to form a first electrical contact, thereby forming a punched combined sheet;
   (d) punching a second electrically conductive sheet with a punch or punches to form an electrically conductive sheet having a notching opening corresponding to that of the punched combined sheet and a second contact area in the second electrically conductive sheet, thereby forming an opposite electrode sheet;
   (e) adhering the opposite electrode sheet to the electrically resistive sheet portion of the punched combined sheet with an electrically conductive surface facing the electrically resistive sheet, said opposite electrode sheet being adhered such that the notching opening corresponding to the notching opening in the combined sheet is aligned with the notching opening in the combined sheet, and the second contact area is aligned with the second bound opening, thereby forming an electrochemical sheet, and
   (f) cleaving the electrochemical sheet thereby forming a spent electrochemical sheet and a free electrochemical cell having a sample space for receiving a sample defined by the first and second conductive sheets and the notch in the electrically resistive sheet, and first and second contact areas in electrically-conductive contact with electrode portions of the first and second conductive sheets exposed in the sample space for connection of said first and second electrode portions with a meter.

2. The method of claim 1, further comprising as part of forming the opposite electrode, the step of punching a vent opening through the second electrically conductive sheet of the combined sheet, wherein the vent opening is aligned in the assembled cell with the notch in the electrically resistive sheet to form a passageway to the interior of the space for receiving a sample.

3. The method of claim 2, wherein the vent opening intersects with an end of the first major open area and together with the notching opening defines the length of the sample space.

4. The method of claim 1, further comprising, as part of forming the punched combined sheet, the step of punching a vent opening through the electrically resistive sheet and the first electrically conductive sheet of the combined sheet, wherein the vent opening is aligned with the notch in the electrically resistive sheet to form a passageway to the interior of the space for receiving a sample.

5. The method of claim 4, further comprising as part of forming the opposite electrode, the step of punching a vent opening through the second electrically conductive sheet of the combined sheet, wherein the vent opening is aligned in the assembled cell with the notch in the electrically resistive sheet to form a passageway to the interior of the space for receiving a sample.

6. The method of claim 4, wherein the vent opening intersects with an end of the first major open area and together with the notching opening defines the length of the sample space.

7. The method of claim 1, further comprising the step of adding a reagent to the sample space.

8. The method of claim 7, wherein the reagent is added to the notch in the punched combined sheet prior to formation of the electrochemical sheet.

9. The method of claim 8, wherein the reagent comprises an enzyme and a redox mediator.

10. The method of claim 9, wherein the enzyme is glucose oxidase.

11. The method of claim 1, wherein the first and second electrically conductive sheets comprise gold.

12. The method of claim 1, wherein the bound openings in the electrically resistive sheet are of rectilinear cross-section.

13. The method of claim 1, wherein the electrically resistive sheet and the first and second electrically conductive sheets are each provided with aligned registration holes for manufacturing alignment, said registration holes being located in the portion of the sheets that is cleaved off as the spent electrochemical sheet, such that they do not become part of the final device.

14. The method of claim 1, wherein the electrically resistive sheet has a thickness, and the notch has dimensions such that the space for receiving a sample has volume of less than 1 µl.

15. The method of claim 1, wherein two bound openings are formed in the resistive sheet.

16. The method of claim 1, wherein the opposite electrode has two opposing conductive surfaces, and wherein both sides of the opposite electrode are adhered to a combined punched sheet to form a device with two stacked sample receiving spaces.

17. The method of claim 1, wherein a plurality of bound openings are formed in the electrically resistive sheet, whereby a plurality of coplanar sample receiving spaces are formed.

18. The method of claim 1, wherein the electrically resistive sheet has a thickness, and the notch has dimensions such that the space for receiving a sample has volume of less than 0.5 µl.

* * * * *